(12) United States Patent
Burkhardt et al.

(10) Patent No.: US 7,939,036 B2
(45) Date of Patent: May 10, 2011

(54) CUVETTE HOLDER, CUVETTE ARRAY AND ANALYZER COMPRISING SUCH COMPONENTS

(75) Inventors: Claudius Burkhardt, Lucerne (CH); Gottlieb Schacher, Kriens (CH); Renato Belz, Emmenbrücke (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 644 days.

(21) Appl. No.: 11/523,837

(22) Filed: Sep. 20, 2006

(65) Prior Publication Data

US 2008/0095666 A1 Apr. 24, 2008

(30) Foreign Application Priority Data

Sep. 21, 2005 (EP) ..................... 05077156

(51) Int. Cl.
*B01L 9/06* (2006.01)
*G01N 21/00* (2006.01)
*G01N 31/00* (2006.01)
*G01N 33/00* (2006.01)

(52) U.S. Cl. ............. 422/561; 422/560; 422/63; 422/64

(58) Field of Classification Search ........... 422/560–561
See application file for complete search history.

(56) References Cited

U.S. PATENT DOCUMENTS

| 4,126,418 | A | * | 11/1978 | Krasnow | ........................ 422/64 |
| 5,098,663 | A | | 3/1992 | Berthold et al. | |
| 5,246,665 | A | * | 9/1993 | Tyranski et al. | ............... 422/64 |
| 5,384,094 | A | | 1/1995 | Schacher et al. | |
| 5,571,479 | A | * | 11/1996 | Koch | ............................ 422/102 |
| 5,579,929 | A | | 12/1996 | Schwartz et al. | |
| 5,948,691 | A | * | 9/1999 | Ekiriwang et al. | ............ 436/183 |
| 6,355,488 | B1 | | 3/2002 | Rousseau et al. | |

FOREIGN PATENT DOCUMENTS

| EP | 0 542 319 A1 | 5/1988 |
| JP | 63292064 A | 11/1988 |
| JP | 2000-517064 | 12/2000 |

* cited by examiner

*Primary Examiner* — Jill Warden
*Assistant Examiner* — Charles Hammond
(74) *Attorney, Agent, or Firm* — Dinsmore & Shohl LLP

(57) ABSTRACT

A cuvette holder for holding a plurality of reaction cuvettes is disclosed. The cuvette holder includes a body made by injection molding of a plastic material. The body extends along a circular segment and defines an array of chambers arranged along a circular segment, each of the chambers is for receiving, retaining and loosely holding the upper end portion of a reaction cuvette.

8 Claims, 15 Drawing Sheets

CUVETTE HOLDER, CUVETTE ARRAY AND ANALYZER COMPRISING SUCH COMPONENTS

RELATED APPLICATIONS

This application claims priority to EP 05077156.7 filed Sep. 21, 2005.

FIELD OF THE INVENTION

The invention concerns a cuvette holder for holding a plurality of reaction cuvettes. The invention concerns a cuvette array comprising such a cuvette holder. The invention further concerns an analyzer comprising such a cuvette holder and cuvette array.

BACKGROUND

In automatic analyzers, and in particular in clinical chemistry analyzers of the type comprising a conveyor for transporting reaction cuvettes adapted for receiving sample-reagent mixtures to be analyzed by means of electro-optical measurements, it is advantageous to insert groups of reaction cuvettes into corresponding cavities of the conveyor, instead of inserting the cuvettes one by one, because the latter procedure is prone to damage at least a part of the cuvettes used, the damage to be expected being in particular damage to the parts of the reaction cuvettes which are provided with the optical properties suitable for the measurements. Such damage would render questionable the accuracy and reliability of the electro-optical measurement of the cuvettes' contents.

Known cuvette holders are made by injection molding and are designed in such a way that they tightly hold the cuvettes and thereby influence the position of the cuvettes even after they have been inserted into respective cavities of a conveyor. The latter influence of the cuvette holder interferes with and modifies the position actually taken by each cuvette inserted into a cavity. This is undesirable, because deformations and manufacturing tolerances of both the cuvette holder and the cuvettes held by the holder affect the position of each cuvette in a non-uniform, unpredictable way and prevents positioning of the cuvettes in their optically optimum positions in the cavities, i.e. in positions which are favorable for carrying out reliable electro-optical, e.g. photometric measurements of the cuvette contents.

Cuvette arrays as known in the prior art are either an assembly of a cuvette holder of the above-mentioned type and a plurality of cuvettes held by the cuvette holder or are arrays of cuvettes made by injection molding as a single-piece component. Both these types of cuvette arrays have the same above mentioned drawbacks.

The use of the above mentioned known cuvette holders and cuvette arrays in known automatic analyzers negatively affect the analyzer performance due to the drawbacks described above.

SUMMARY OF THE INVENTION

A first aim of the invention is to provide a cuvette holder of the above mentioned kind that makes possible to avoid the above-mentioned drawbacks of known cuvette holders. According to a first aspect of the invention the above aim is achieved by means of a cuvette holder for holding a plurality of reaction cuvettes, said cuvette holder comprising a body made by injection molding of a plastic material, said body extending along a circular segment and defining an array of chambers arranged along a circular segment, each of said chambers having an upper opening, a lower opening, and flexible tongues which extend from said upper opening towards the interior of said chamber, the flexibility of said flexible tongues allowing insertion of an entire reaction cuvette through said upper opening, the arrangement of said flexible tongues within said chamber preventing withdrawal of the cuvette through said upper opening, said lower opening of said chamber having a cross-section which is large enough for allowing passage of the body of said cuvette through said lower opening, but which prevents passage of said upper portion of said cuvette through said lower opening, each of said chambers being thereby adapted for receiving, retaining and loosely holding the upper end portion of a reaction cuvette.

A second aim of the invention is to provide a cuvette array that makes possible to avoid the above-mentioned drawbacks of cuvette arrays known in the prior art. According to a second aspect of the invention the above aims are achieved by means of a cuvette array comprising a cuvette holder as just described and a plurality of reaction cuvettes, the upper end portion of each of said cuvettes being loosely held by said cuvette holder.

A third aim of the invention is to provide an analyzer that makes possible to avoid the above-mentioned drawbacks of analyzers known in the prior art. According to a third aspect of the invention the above aims are achieved by means of an analyzer comprising a rotatable conveyor for conveying reaction cuvettes along a circular path, said conveyor having a first ring shaped body having a circular array of cavities, each cavity being adapted for receiving a single reaction cuvette, and at least one cuvette array as just described.

The main advantages obtained with a cuvette holder, cuvette array, and analyzer according to the invention is that each of the reaction cuvettes is placed in a cavity of the conveyor in an optically optimum position, i.e. in a position which is favorable for carrying out reliable electro-optical, e.g. photometric measurements of the cuvette contents. This is made possible mainly by the fact that the cuvette holder according to the invention loosely holds the cuvettes before they are installed in the conveyor and exerts no influence on the position of any cuvette in its respective cavity when the cuvettes are installed in the conveyor.

BRIEF DESCRIPTION OF THE DRAWINGS

The subject invention will now be described in terms of its preferred embodiments with reference to the accompanying drawings. These embodiments are set forth to aid the understanding of the invention, but are not to be construed as limiting.

Figure 15:
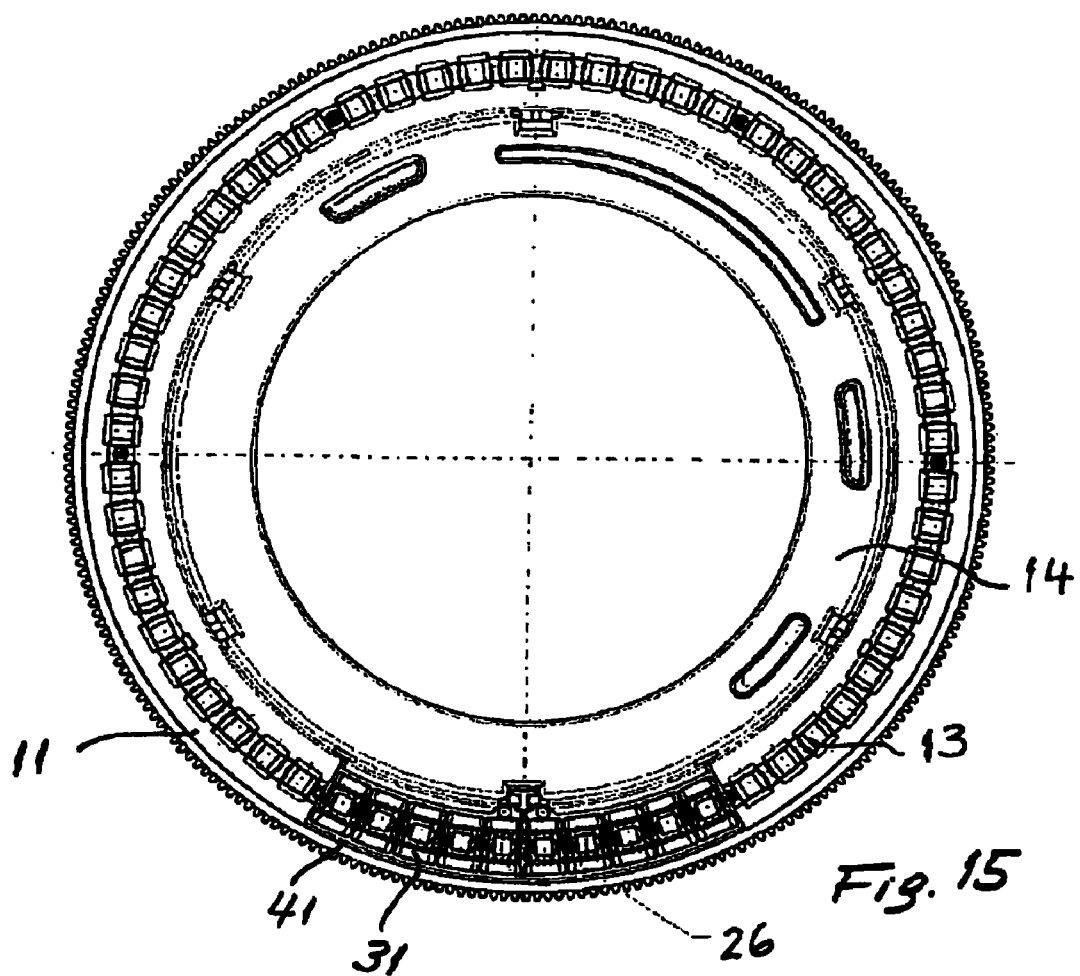
FIG. 15 shows a top plan view of conveyor 11 shown in FIG. 2 and of an array of reaction cuvettes 31 inserted in respective cavities 13 of conveyor 11.
Figure 17:
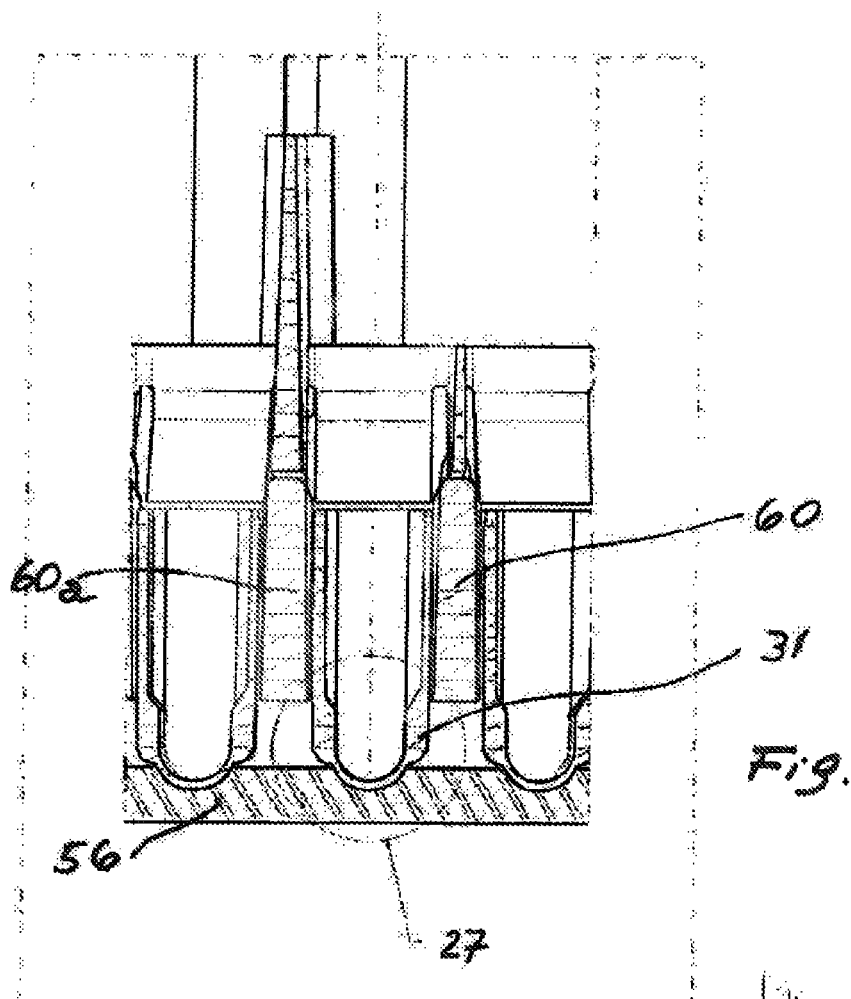
FIG. 17 shows a cross-sectional view taken along a plane E-E in FIG. 16 of cuvettes 31 inserted in respective cavities of conveyor 11.
Figure 19:
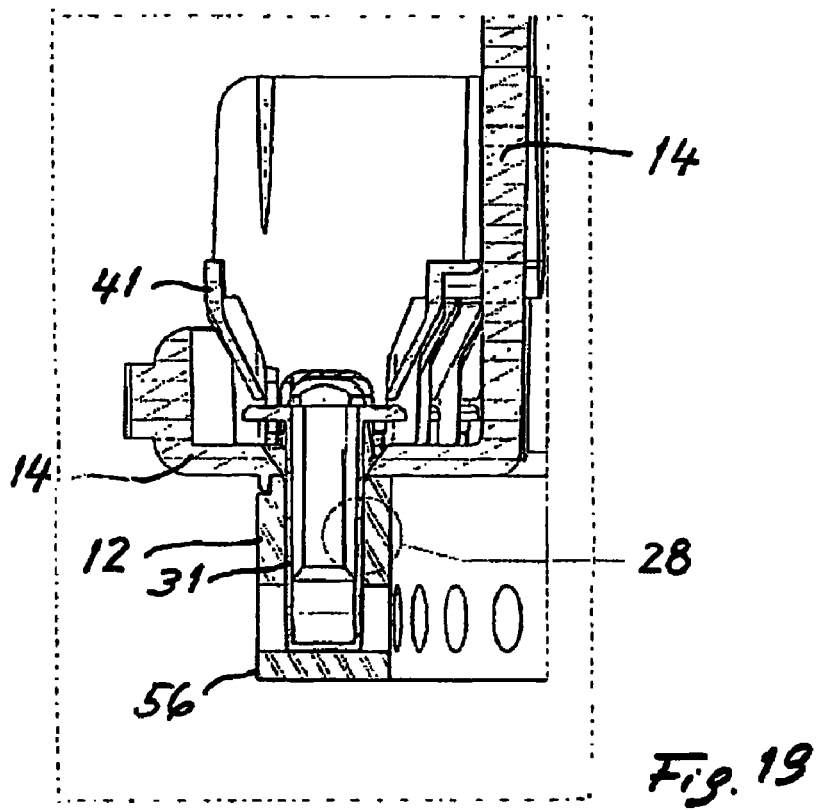
FIG. 19 shows a cross-sectional view taken along a plane F-F in FIG. 16 of a cuvette 31 inserted in a cavity of conveyor 11.
Figure 27:
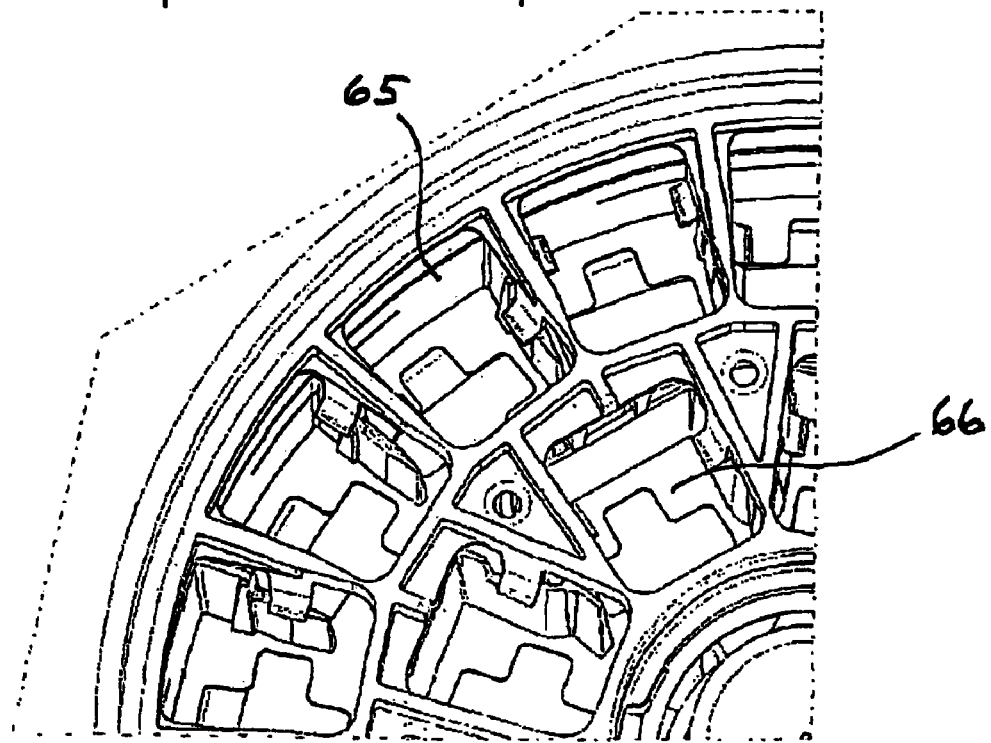
FIG. 27 shows an enlarged view of a portion of FIG. 26.
Figures 29, 30:
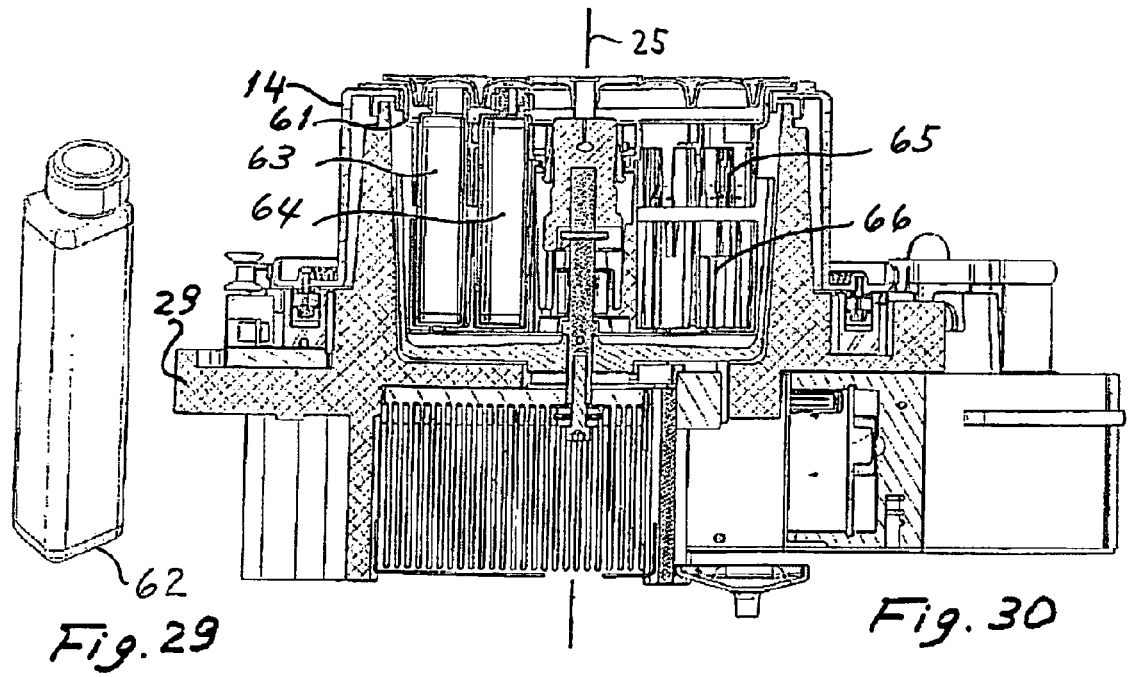
FIG. 29 shows a perspective view of a single reagent container.
FIG. 30 shows a cross-sectional view taken along a plane I-I in FIG. 28.
Figure 28:
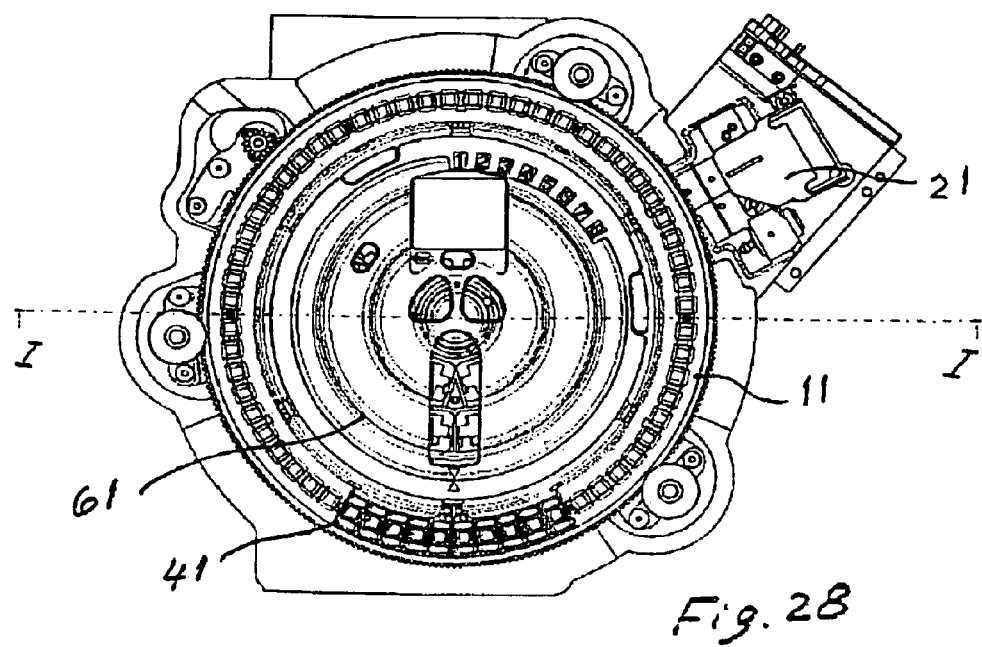
FIG. 28 shows a top view of the conveyor part of the analyzer shown in FIG. 1 and in particular reagent container assembly 61 before it is loaded with reagent containers.

REFERENCE NUMERALS USED IN DRAWINGS 11 conveyor
12 first ring shaped body
13 cavity for receiving a reaction cuvette
14 second ring shaped body
15 wall of second ring shaped body
16 opening
17 first chamber (within second ring shaped body)
18 sample tube area
19 cavity for receiving a sample tube
20 thermal block
21 photometer
22 rotor driving means
23 washing station
24 path of light beam of photometer
25 rotation axis of conveyor 11
26 portion of FIG. 15
27 portion of FIG. 17
28 portion of FIG. 19
29 thermal insulation layer
31 reaction cuvette
32 body of cuvette 31
33 lower end portion of cuvette 31
34 upper end portion of cuvette 31
35 bottom wall of cuvette 31
36 opening of cuvette 31
37 tongue member
38 tongue member
39 length symmetry axis of cuvette 31
40 tongue
41 cuvette holder
42 body of cuvette holder
43 chamber of cuvette holder
44 connecting part/guiding rib
45 upper frame
46 lower frame
47 side wall
48 side wall
49 intermediate wall
50 tongue
51 bucket/hollow body
52 bottom wall of bucket
53 side walls of bucket
54 second chamber within bucket
55 air gap
56 bottom wall of cavity 13
57 depression in inner surface of bottom wall 56
58 edge
59 edge
60 intermediate wall
60a intermediate wall
61 reagent container assembly
62 reagent container
63 reagent container
64 reagent container
65 chamber for receiving a reagent container
66 chamber for receiving a reagent container
71 automatic pipetting device
72 pipetting needle
73 rail of transport device of pipetting needle

DETAILED DESCRIPTION OF THE INVENTION

Preferred embodiments are described hereinafter with reference to the accompanying drawings.

Example of an Analyzer

Figure 1:
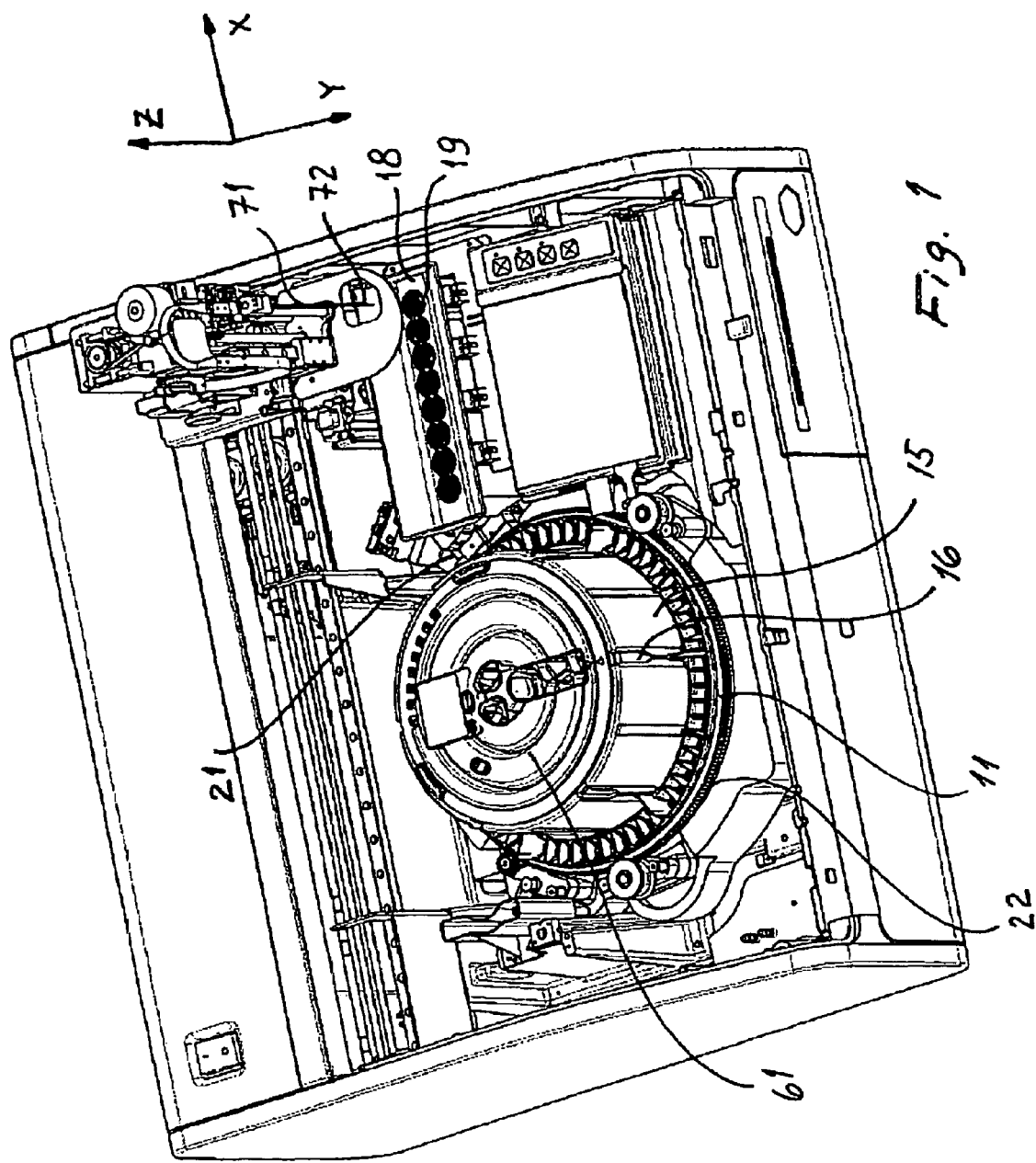
FIG. 1 shows a perspective view of an analyzer according to the invention.

As shown by FIG. 1 an analyzer according to the invention, e.g. a clinical-chemistry for analyzing sample-reagent mixtures contained in reaction cuvettes. The analyzer shown in FIG. 1 comprises a rotatable conveyor 11 for conveying reaction cuvettes 31 inserted in corresponding cavities of that conveyor along a circular path, at least one array of reaction cuvettes 31, a hollow body 51 (shown in FIG. 25) arranged in the central part of conveyor, a reagent container assembly 61 installed in a cavity 54 of hollow body 51, a sample tube area 18 located adjacent to conveyor 11, an automatic pipetting device 71, a photometer 21 located adjacent to conveyor 11, and conveyor driving means 22 for rotating conveyor 11.

Figure 3:
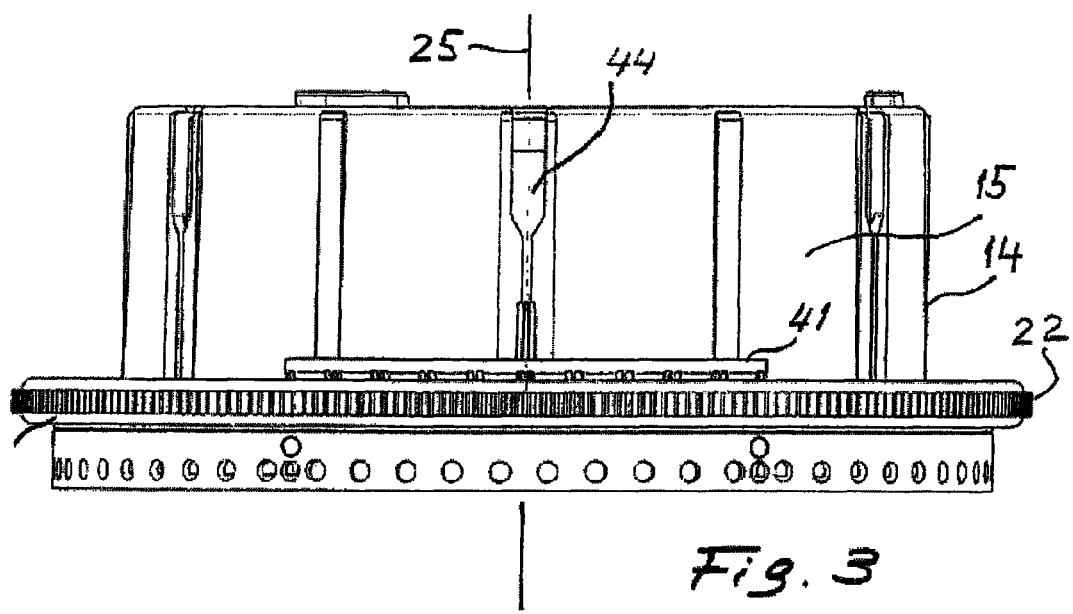
FIG. 3 shows a side view of conveyor 11 in FIG. 1.

FIG. 3 shows the rotation axis 25 of conveyor 11.

Reaction cuvettes 31 inserted in the above mentioned cavities of conveyor 11 are loosely held by a cuvette holder 41 described hereinafter in particular with reference to FIGS. 4 to 20. Such a cuvette holder 41 loosely holds a plurality of reaction cuvettes 31. A cuvette holder 41 and reaction cuvettes 31 held by cuvette holder 41 form a cuvette array. The analyzer comprises at least one such array. Usually reaction cuvettes of a plurality of such cuvette arrays are installed in corresponding cavities of conveyor 11. In the example shown by FIG. 1, conveyor 11 has cavities for receiving 60 reaction cuvettes distributed in 6 cuvette arrays each array having 10 reaction cuvettes.

Figure 2:
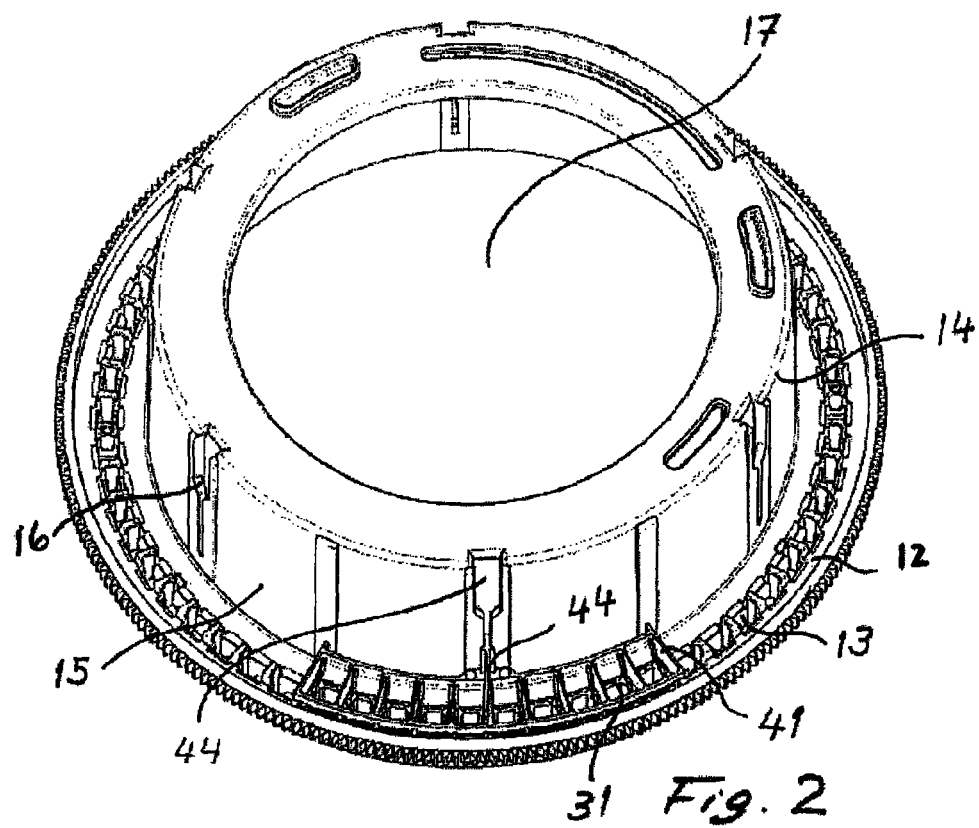
FIG. 2 shows a perspective view of conveyor 11 in FIG. 1.

Cuvette holder 41 serves for holding an array of reaction cuvettes 31. Cuvette holder 41 has a connecting part 44 which is adapted for inserting it into an opening 16 of wall 15 of the conveyor, thereby connecting cuvette holder 41 to conveyor 11. As shown by FIG. 2, the relative position of the connecting part 44 and the opening 16 of wall 15 are such that when connecting part 44 is inserted into opening 16 the reaction cuvettes 31 held by a cuvette holder 41 are inserted into corresponding cavities 13 of a first ring shaped body 12 of conveyor 11.

As shown by FIGS. 2 and 3, conveyor 11 comprises a first ring shaped body 12 and a second ring shaped body 14. First ring shaped body 12 has a circular array of cavities 13, each of which is adapted for receiving a single reaction cuvette 31 of the type described below with reference to FIGS. 8 to 10. Neighboring cavities 13 are separated from each other by intermediate walls like walls 60 and 60a shown in FIG. 17. First ring shaped body 12 is preferably made of a suitable metal.

Figure 20:
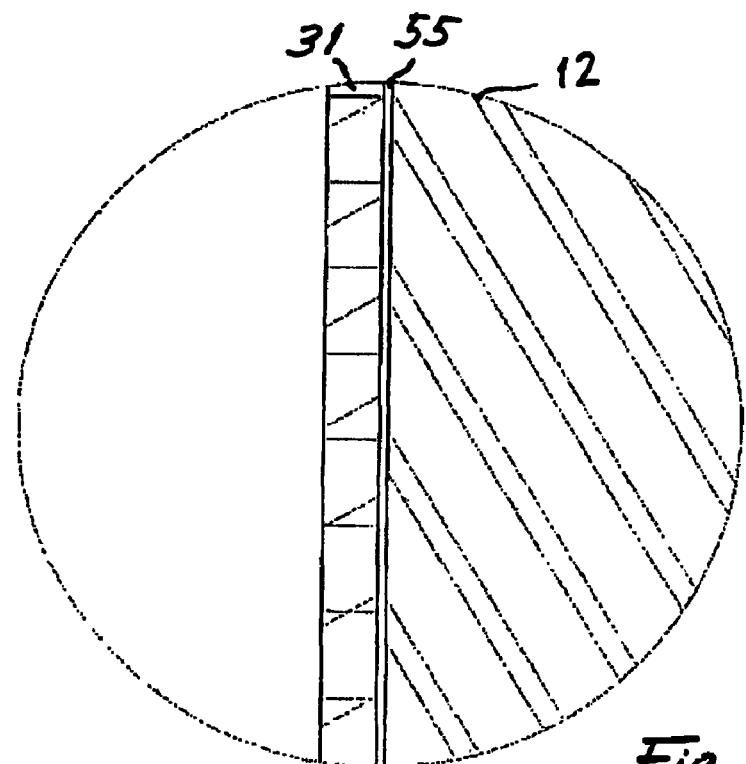
FIG. 20 shows an enlarged view of portion 28 of FIG. 19 showing the air gap between a side wall of a cuvette 31 and a side wall of a cavity of conveyor 11.

The size of each cavity 13 is very close to the size of the reaction cuvette, but as shown by FIGS. 19 and 20 the size of cavity 13 is such that an air gap 55 exists between the outer surface of cuvette 31 and the inner surface of cavity 13 in ring shaped body 12 of conveyor 11. FIG. 19 shows a cross-sectional view taken along a plane F-F in FIG. 16 of a cuvette 31 inserted in a cavity 13 of conveyor 11. FIG. 20 shows an enlarged view of portion 28 of FIG. 19 showing air gap 55 between cuvette 31 and the inner surface of cavity 13. An air gap 55 like the one shown in FIG. 20 preferably exists on all 4 sides of the body 32 of cuvette 31. Air gaps like gap 55 in FIG. 20 facilitate the insertion of the body 32 of cuvette 31 in a cavity 13 of conveyor 11.

Figure 16:
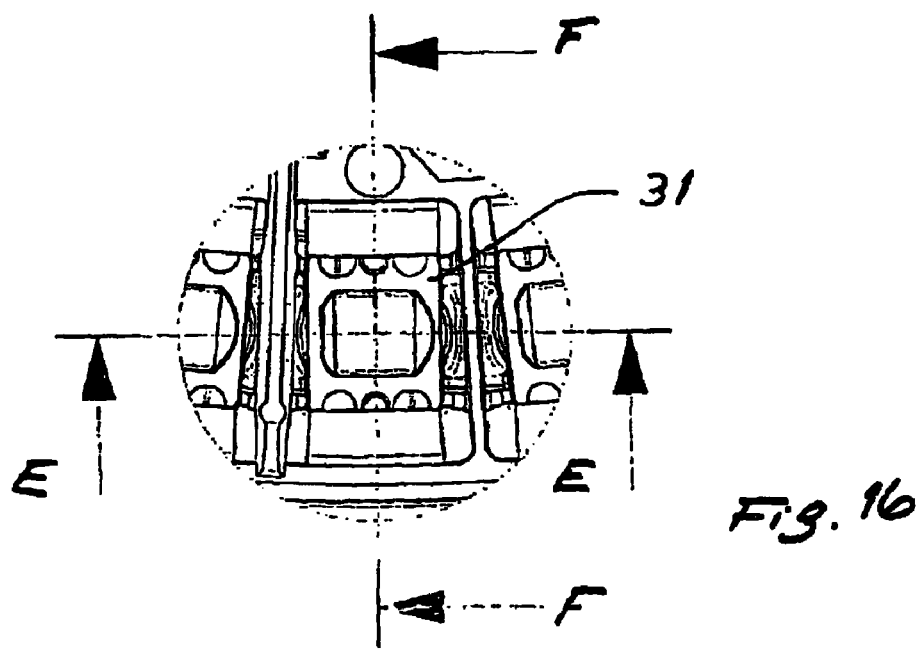
FIG. 16 shows an enlarged view of portion 26 of FIG. 15 showing a top plan view of one of the cuvettes 31 inserted in one of the cavities of conveyor 11.

FIG. 15 shows a top plan view of conveyor 11 shown in FIG. 2 and of an array of reaction cuvettes 31 inserted in respective cavities 13 of conveyor 11. FIG. 16 shows an enlarged view of portion 26 of FIG. 15 showing a top plan view of one of the cuvettes 31 inserted in one of the cavities of conveyor 11.

Figure 18:
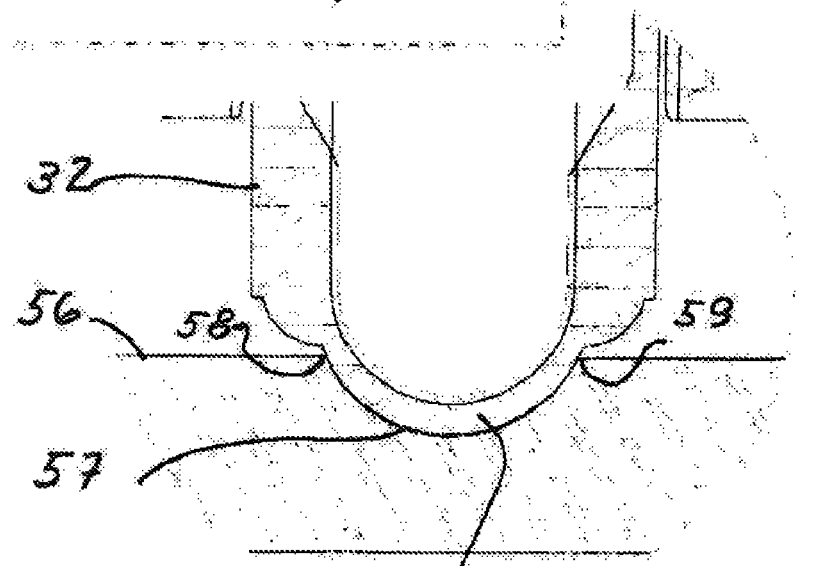
FIG. 18 shows an enlarged view of portion 27 of FIG. 17 showing the contact between the bottom wall of a cuvette 31 and edges of the bottom wall of a cavity of conveyor 11.

FIG. 17 shows a cross-sectional view taken along a plane E-E in FIG. 16 of cuvettes 31 inserted in respective cavities of conveyor 11. FIG. 18 shows an enlarged view of portion 27 of FIG. 17 showing the contact between the bottom wall of a cuvette 31 and edges of the bottom wall of a cavity of conveyor 11.

As shown by FIG. 18, each cavity 13 of ring shaped body 12 of conveyor 11 has a bottom wall 56. Bottom wall 56 has a central depression 57 which approximately matches the shape of the outer surface of the bottom wall 35 of cuvette 31, but in the central zone of depression 57 there is an air gap 55 between the inner surface of depression 57 and the outer surface of cuvette bottom wall 35. The inner surface of bottom wall 56 has two edges 58 and 59 which contact and support the bottom wall of a reaction cuvette 31 inserted and positioned in a cavity 13. Edges 58 and 59 are parallel to each other and both edges are approximately oriented in radial direction with respect to rotation axis 25 of conveyor 11.

Second ring shaped body 14 has a wall 15 which extends upwardly from the inner side of first ring shaped body 12. Wall 15 has openings 16, each of which is adapted for receiving a corresponding connecting part 44 of a cuvette holder 41. Second ring shaped body 14 defines a chamber 17 within the interior of body 14.

Figure 25:
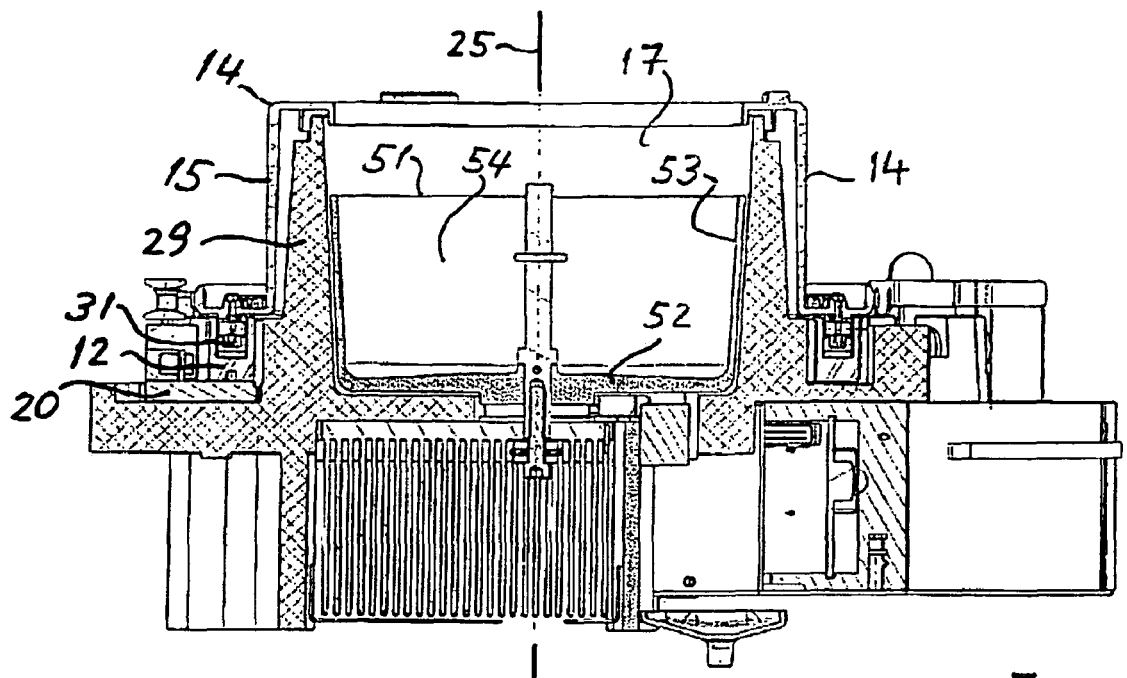
FIG. 25 shows a cross-sectional view taken along a plane H-H in FIG. 24.
Figure 24:
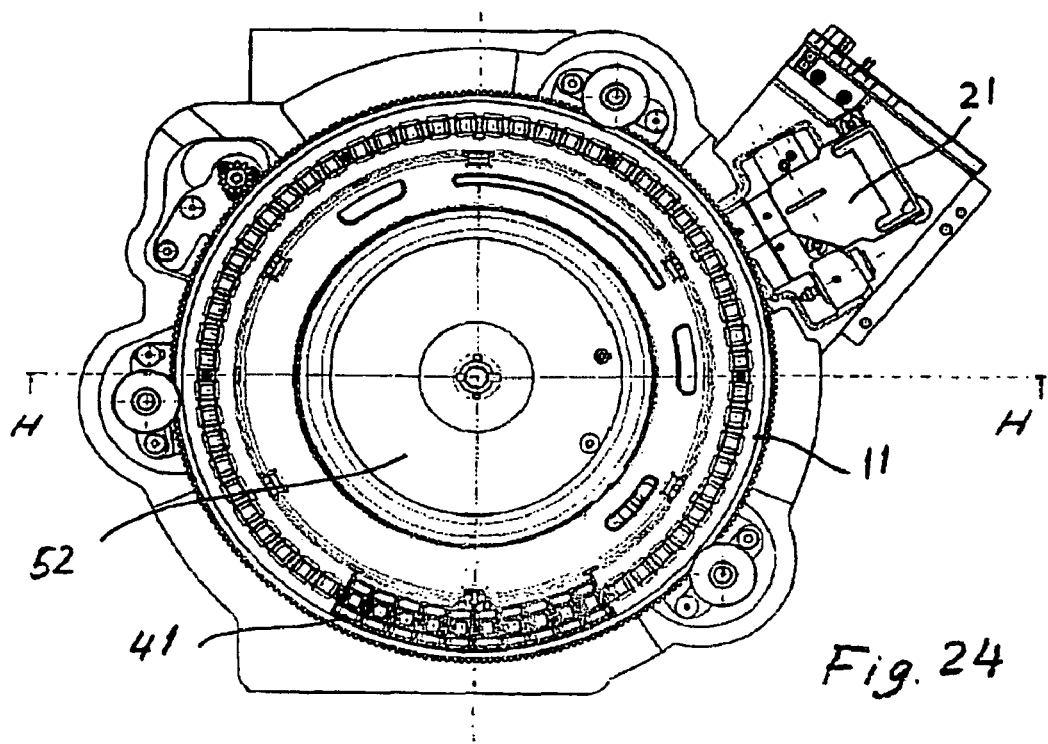
FIG. 24 shows a top view of the conveyor part of the analyzer shown in FIG. 1 when reagent container assembly 61 is removed therefrom.

FIG. 24 shows a top view of the conveyor part of the analyzer shown in FIG. 1 when reagent container assembly 61 is removed therefrom. FIG. 25 shows a cross-sectional view taken along a plane H-H in FIG. 24.

As shown by FIG. 25 a hollow body 51 is arranged in chamber 17 within second ring shaped body 14. Hollow body 51 has e.g. the shape of a bucket, and has a bottom wall 52 and side walls 53 which define a chamber 54.

Figure 23:
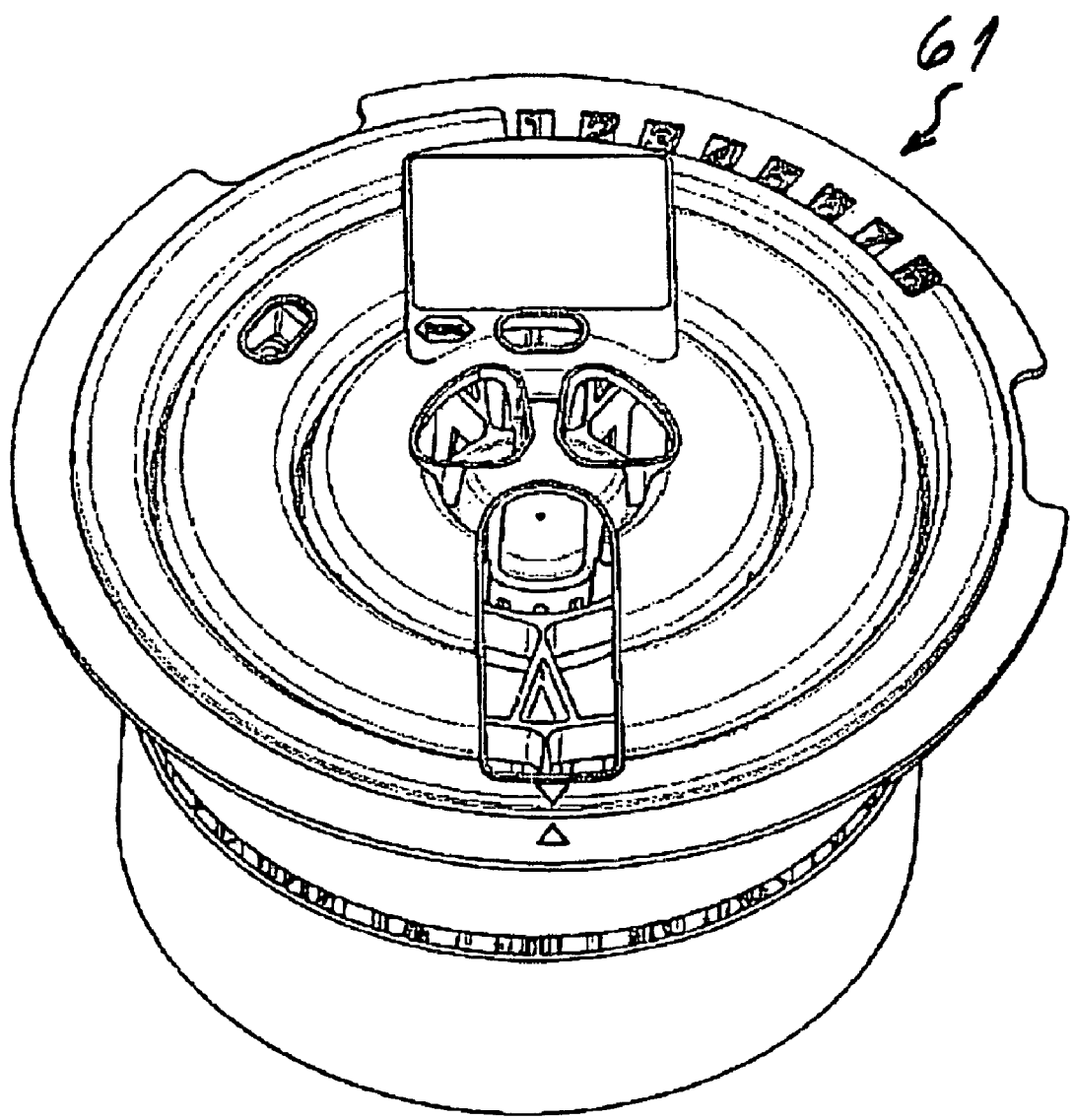
FIG. 23 shows a perspective view of reagent container assembly 61 when it is removed from the analyzer shown in FIG. 1.

FIG. 23 shows a perspective view of reagent container assembly 61 when it is removed from the analyzer shown in FIG. 1. Reagent container assembly 61 is adapted for being positioned with its lower part in chamber 54 of hollow body 51.

Figure 26:
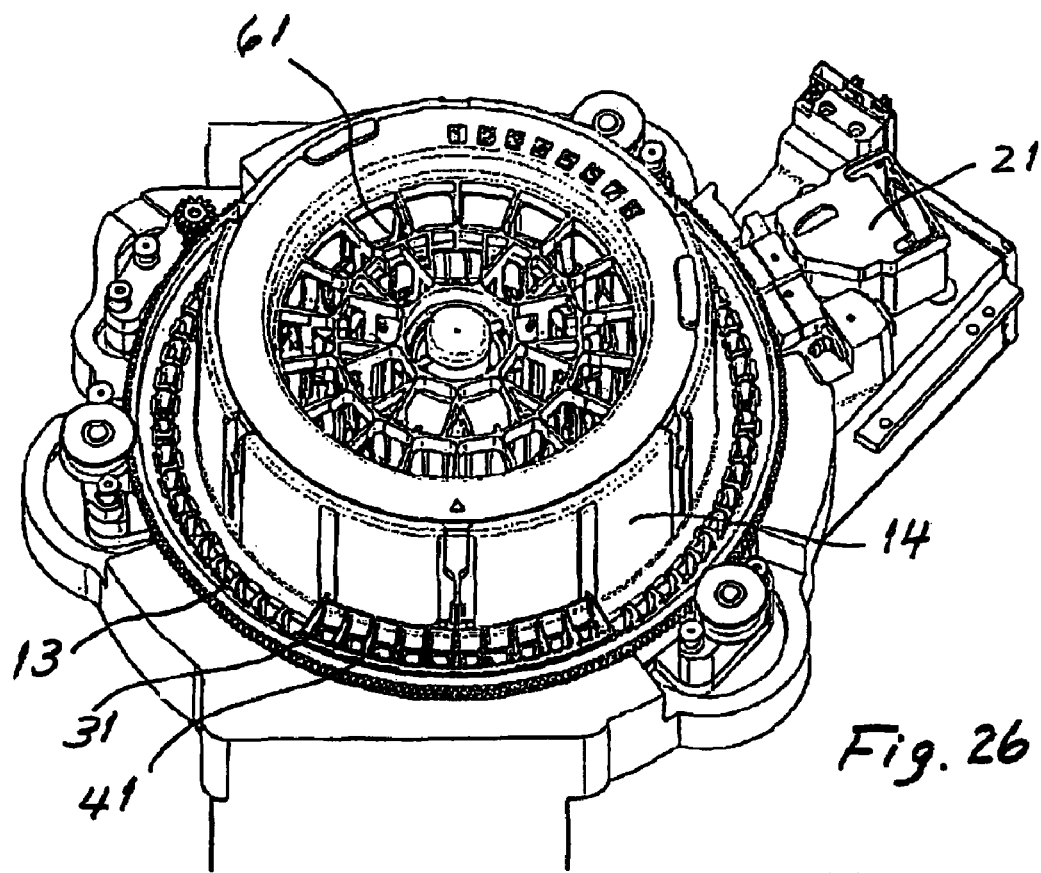
FIG. 26 shows a perspective view of reagent container assembly 61 installed in the analyzer, but without its cover and without any reagent container in it.

FIG. 26 shows a perspective view of reagent container assembly 61 installed in the analyzer, but without its cover and without any reagent container in it. FIG. 27 shows an enlarged view of a portion of FIG. 26.

As can be appreciated from FIGS. 26 and 27 reagent container assembly 61 comprises a housing having two concentric arrays of chambers adapted for receiving reagent containers.

FIG. 28 shows a top view of the conveyor part of the analyzer shown in FIG. 1 and in particular of reagent container assembly 61 before it is loaded with reagent containers.

FIG. 29 shows a perspective view of a reagent container 62.

FIG. 30 shows a cross-sectional view taken along a plane I-I in FIG. 28.

As shown by FIG. 30, reagent container assembly 61 contains a plurality of chambers 65, 66 for receiving reagent containers 63, 64, like reagent container 62 in FIG. 18, each of which contains a specific reagent in liquid form. Each reagent container carries an automatically readable label (not shown), e.g. a barcode label, which identifies the specific reagent contained in the reagent container.

Sample tube area 18 comprises a rack permanently installed in the analyzer. This rack has several cavities 19 and each of these cavities is adapted for receiving a sample tube containing a liquid sample to be analyzed.

Automatic pipetting device 71 is suitable for effecting all pipetting operations in the analyzer, e.g. the pipetting of a sample portion taken from a sample tube in the sample area 18 into a reaction cuvette 31 in conveyor 11 and the pipetting of a reagent volume taken from a reagent container 62 in reagent assembly 61 into a reaction cuvette 31 in conveyor 11. After these pipetting operations the reaction cuvette contains a sample-reagent-mixture.

Automatic pipetting device 71 comprises a removably mounted pipetting needle 72 and a transport device mounted on a rail 73 which extends in the X-direction shown in FIG. 1. This transport device moves the pipetting needle 72 in two ways: along a rectilinear path in the X-direction, e.g. for bringing pipetting needle 72 to a pipetting position, and along a circular path, e.g. when the tip of pipetting needle 72 is immersed in a liquid contained in a reaction cuvette. The latter circular movement of the pipetting needle 72 is achieved by means of an excenter mechanism which is part of the above-mentioned transport device of pipetting needle 72. The excenter mechanism is adapted for moving the tip of pipetting needle along a circular path, but keeping the length axis of pipetting needle 72 in the Z-direction shown in FIG. 1. This circular motion of the pipetting needle is used e.g. for mixing in a reaction cuvette 31 a liquid sample and a reagent which have been pipetted into the reaction cuvette. For this mixing purpose the circular motion of pipetting needle 72 is effected with the tip of the pipetting needle partially immersed in the sample-reagent-mixture contained in a reaction cuvette 31.

Figure 31:
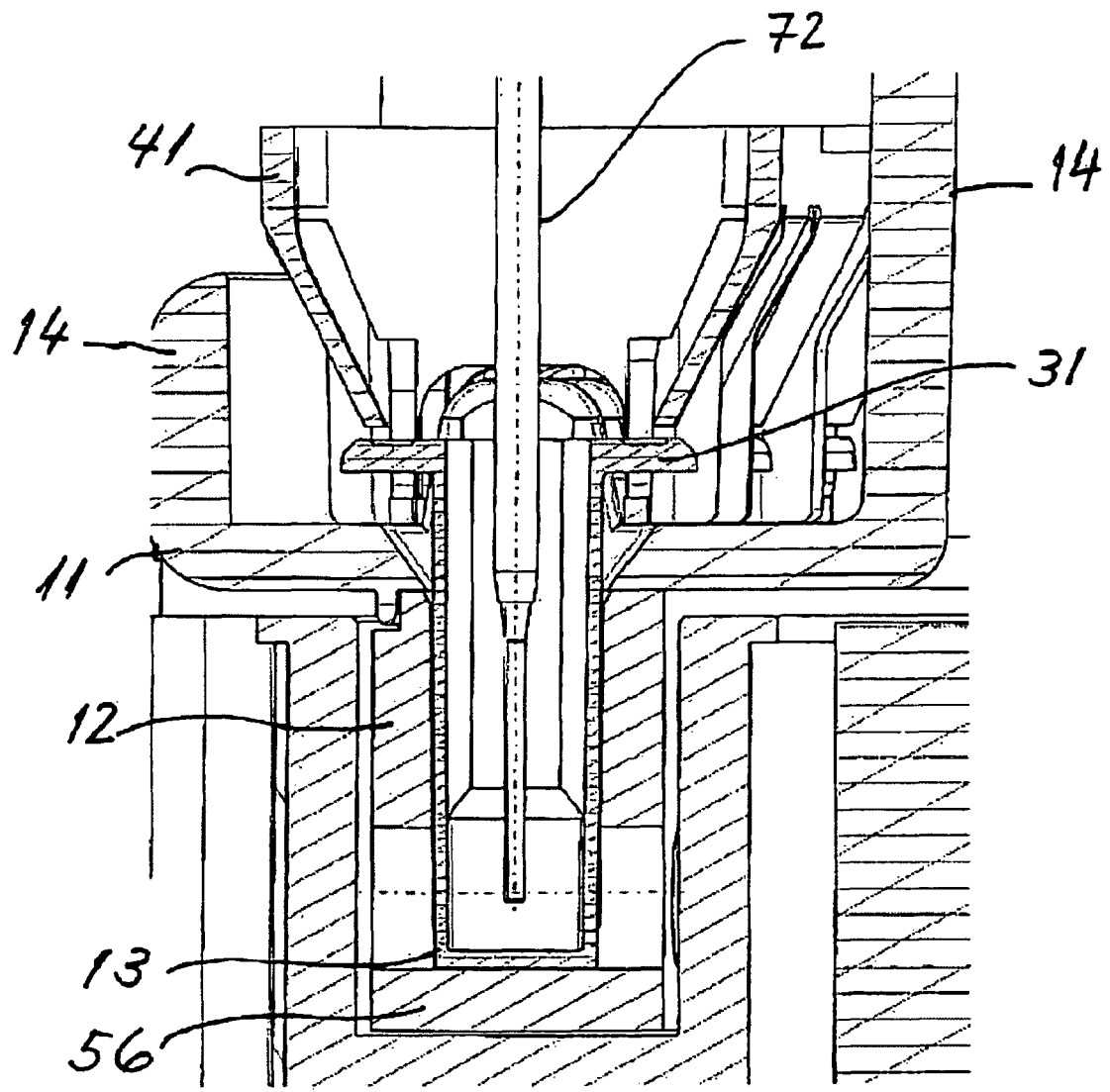
FIG. 31 shows a cross-sectional view of a reaction cuvette 31 and of a pipetting needle 72 positioned therein.

FIG. 31 shows a cross-sectional view of a reaction cuvette 31 inserted in a cavity 13 of conveyor 11 and of a pipetting needle 72 positioned therein.

Figure 21:
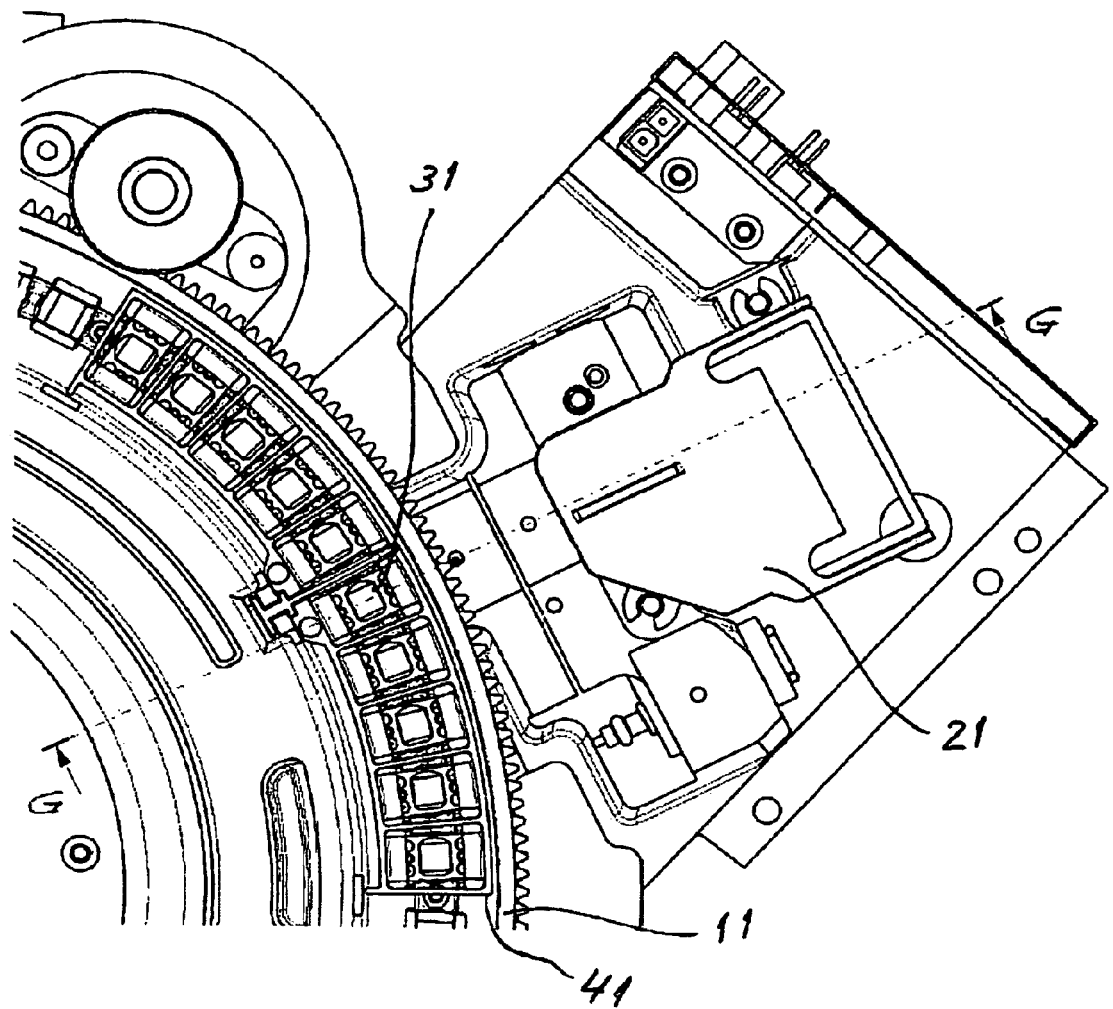
FIG. 21 shows a top plan view of conveyor 11 and photometer 21 (shown in FIG. 1) showing in particular the arrangement of the photometer 21 with respect to the conveyor 11 and a cuvette placed in the path of the light beam emitted by the light source of the photometer.
Figure 22:
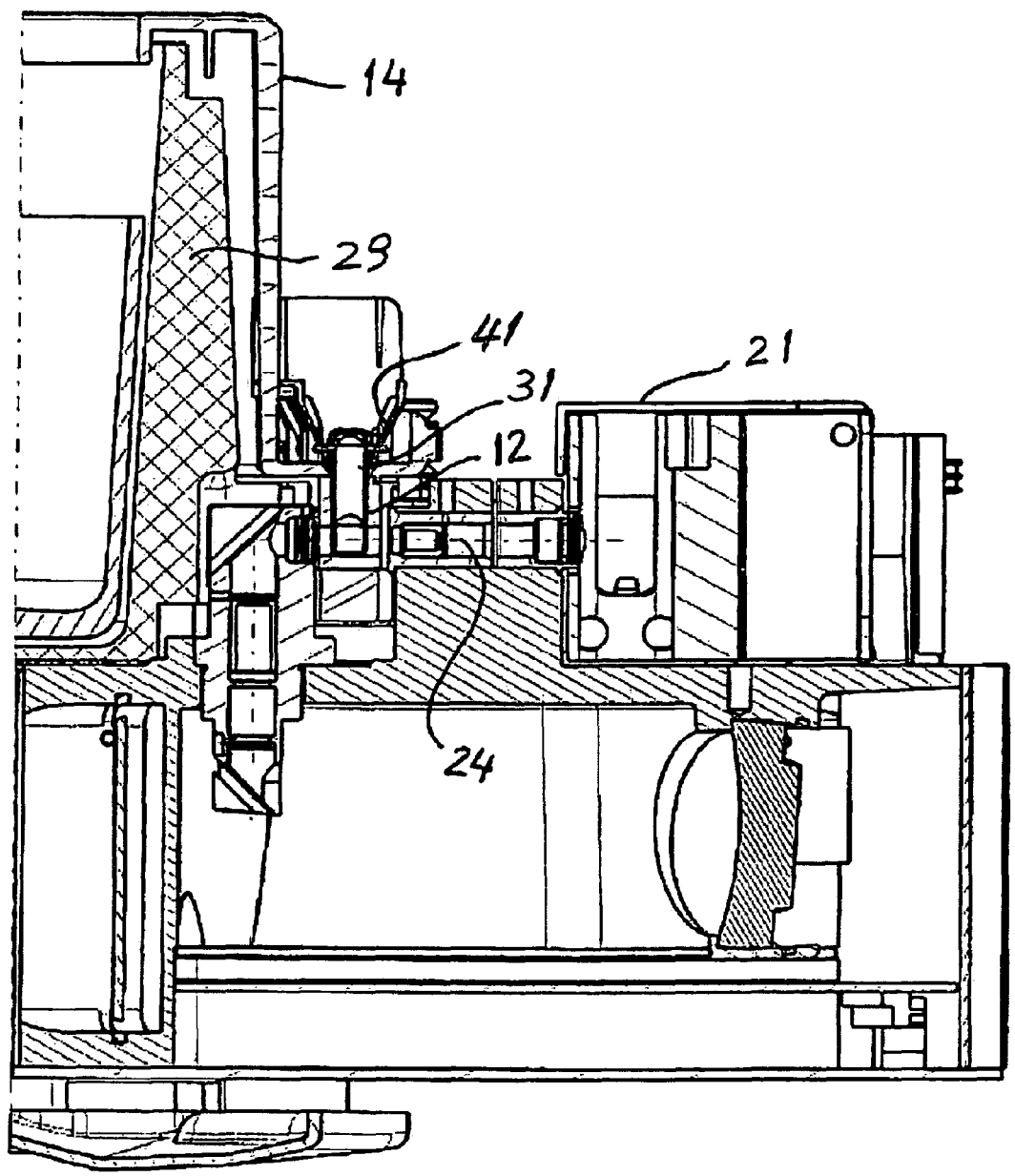
FIG. 22 shows a cross-sectional view taken along a plane G-G in FIG. 21 showing the cuvette placed in the path of the light beam emitted by the light source of the photometer.

As shown by FIGS. 1, 21, 22, 24, 26, 28, photometer 21 is located adjacent to conveyor 11 for carrying out photometric measurements of liquid sample-reagent-mixtures contained in reaction cuvettes 31. For this purpose the driving means 22 of conveyor 11 rotate the conveyor step-wise for accurately positioning each reaction cuvette 31 in the optical path 24 of the light beam of photometer 21 so that the latter light beam passes through the center of the lower part of the cuvette which contains the sample-reagent-mixture to be measured with photometer. This positioning of a reaction cuvette 31 with respect to the light beam of photometer 21 is shown in FIGS. 21 and 22.

Conveyor driving means comprise means for rotating conveyor 11 in a step-wise manner. Conveyor driving means comprise e.g. a belt-drive (not shown) which drives a toothwheel 22 of conveyor 11 and other suitable means for positioning conveyor 11 in accurate angular positions suitable for performing accurate photometrical measurements of the sample-reagent mixture contained in each of the reaction cuvettes 31.

The analyzer shown in FIG. 1 also comprises electrical and electronic components as well as hardware and software for controlling the operation of the analyzer and all components thereof whose operation has to be controlled and coordinated, e.g. the operation of the automatic pipetting device 71, the photometer 21, the management of the samples and reagents present in the analyzer, and the evaluation and display of analysis results and related information.

Example of a Reaction Cuvette

Figure 8:
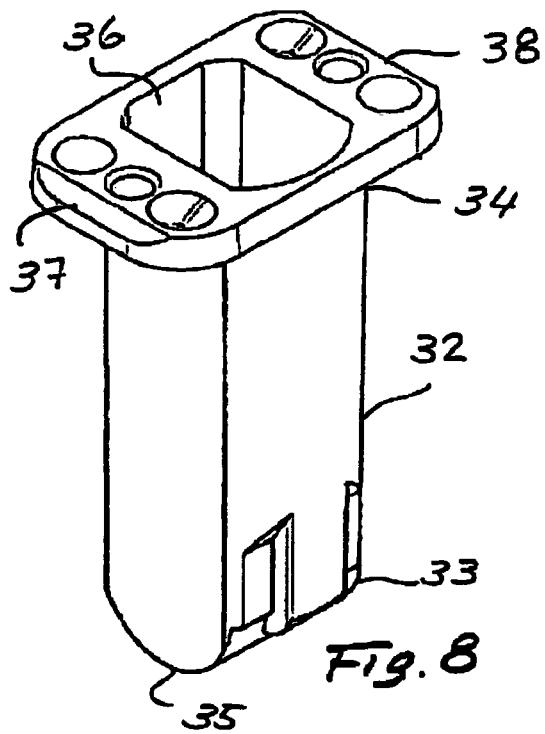
FIG. 8 shows a perspective view of a reaction cuvette 31 of the type which is preferably used with a cuvette holder 41 according to the invention.
Figure 9:
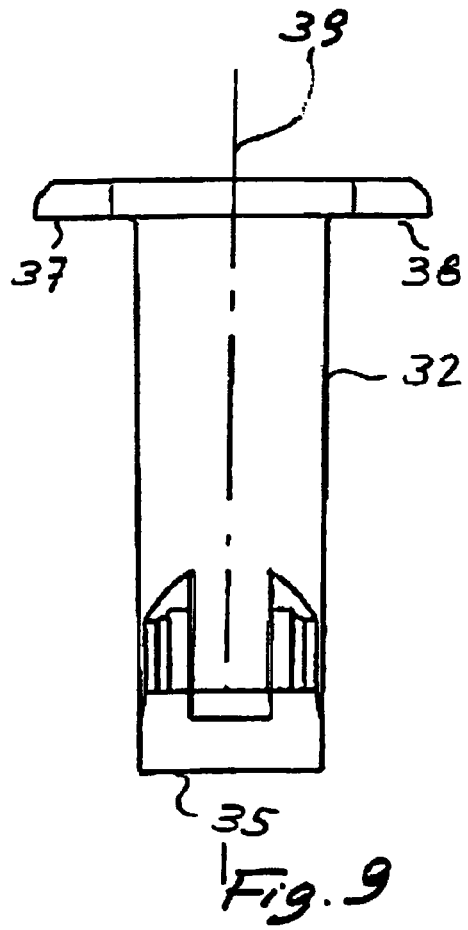
FIG. 9 shows a first side view of reaction cuvette 31 in FIG. 8.
Figure 10:
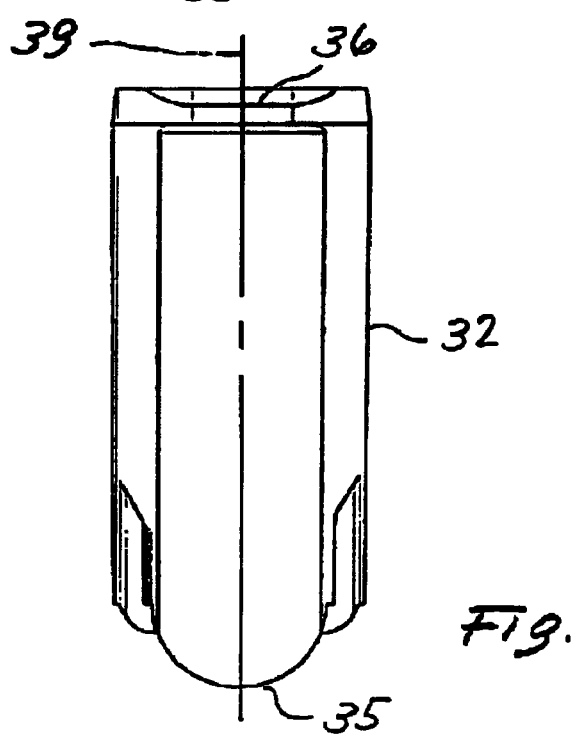
FIG. 10 shows a second side view of reaction cuvette 31 in FIG. 8.

FIG. 8 shows a perspective view of a reaction cuvette 31 of the type which is preferably used with a cuvette holder 41 according to the invention. FIG. 9 shows a first side view of reaction cuvette 31 in FIG. 8. FIG. 10 shows a second side view of reaction cuvette 31 in FIG. 8. Reaction cuvette 31 is a single-piece, disposable component made by injection molding of a plastic material which is suitable for performing photometric measurements of a sample-reagent mixture contained in reaction cuvette 31.

When a reaction cuvette 31 is inserted in a cavity of conveyor 11 it is in vertical position.

As shown by FIGS. 8 to 10, reaction cuvette 31 has a rectilinear tubular body 32 which extends between a lower end portion 33 and an upper end portion 34 which lie at opposite ends of tubular body 32. Lower end portion 33 is closed by a bottom wall 35. Upper end portion 34 ends in an opening 36. In a preferred embodiment upper end portion includes two rigid tongue members 37, 38 adjacent to opening 36 of upper end portion 34. Tongue members 37, 38 extend outwardly from second end portion 34 of the tubular body 32 in opposite directions. Reaction cuvette 31 has a length symmetry axis 39.

Example of a Cuvette Holder

An embodiment of a cuvette holder 41 according to the invention is described hereinafter with reference to FIGS. 4 to 7.

Figure 4:
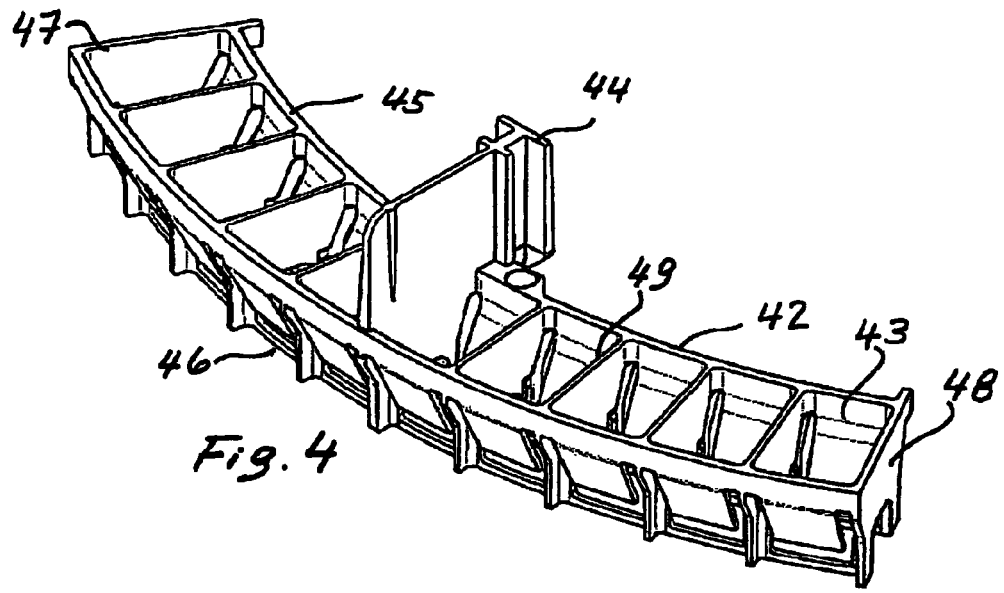
FIG. 4 shows a perspective view of a cuvette holder 41 (shown in FIG. 2) according to the invention.
Figures 6, 7:
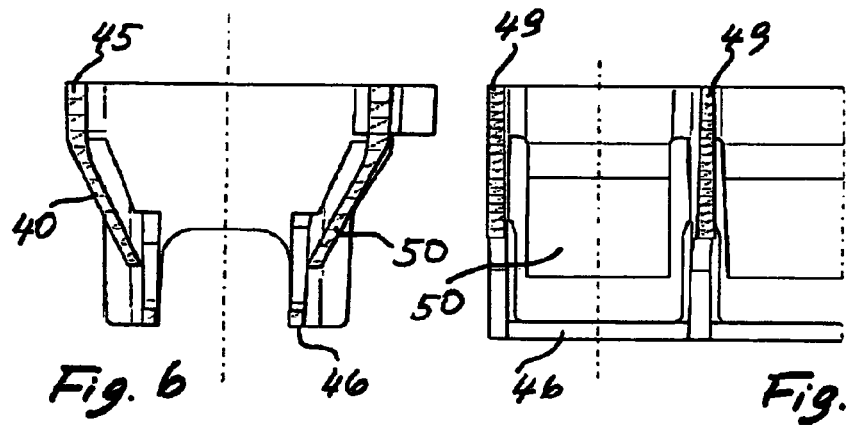
FIG. 6 shows a cross-sectional view taken along a plane A-A in FIG. 5 of a chamber of cuvette holder 41.
FIG. 7 shows a cross-sectional view taken along a plane B-B in FIG. 5 of a chamber of cuvette holder 41.
Figure 5:
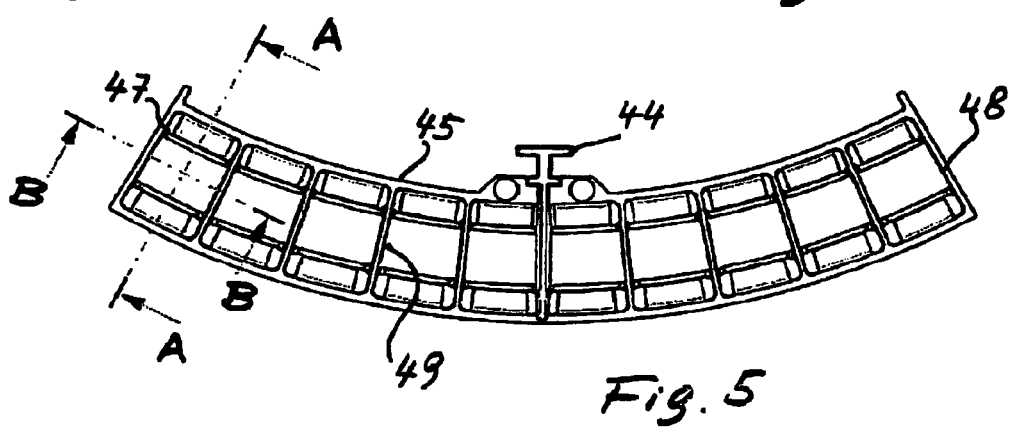
FIG. 5 shows a top plan view of cuvette holder 41 shown in FIG. 4.

FIG. 4 shows a perspective view of a cuvette holder 41 (shown in FIG. 2). FIG. 5 shows a top plan view of cuvette holder 41 shown in FIG. 4. FIG. 6 shows a cross-sectional view taken along a plane A-A in FIG. 5 of a chamber of cuvette holder 41. FIG. 7 shows a cross-sectional view taken along a plane B-B in FIG. 5 of a chamber of cuvette holder 41.

Cuvette holder 41 is configured and dimensioned for loosely holding a plurality reaction cuvettes 31 of the type described above with reference to FIGS. 8 to 10.

Cuvette holder 41 has a body 42 made by injection molding of a plastic material. Body 42 extends along a circular segment and defines an array of chambers 43 arranged along a circular segment. Each of chambers 43 is adapted for receiving, retaining and loosely holding the upper end portion 34 of a reaction cuvette 31.

In a preferred embodiment, the body 42 of cuvette holder 41 is an integrally made, single-piece, disposable component made by injection molding of a suitable plastic material. Body 42 comprises the following portions:

an upper frame 45,
a lower frame 46,
side walls 47, 48 each of which connect an end of upper frame 45 with one end of lower frame 46,
a plurality of intermediate walls 49 which separate neighboring chambers 43 from each other, and
flexible tongues 40, 50 which extend from the upper frame 45 towards the interior of each chamber 43 and which are inclined with respect to a vertical axis passing through the center of a chamber 43.

Each of intermediate walls 49 is radially oriented, i.e. it lies in a plane that passes through the rotation axis 25 of conveyor 11, and connects upper frame 45 with lower frame 46.

The shape and dimensions of frame portions 45 and 46 are such that the array of chambers 43 of cuvette holder 41 closely corresponds to the array of cavities 13 of conveyor 11.

The space available for the upper end portion 34 of a reaction cuvette 31 in each chamber 43 of cuvette holder 41 is delimited by intermediate walls 49 which are the side walls of each chamber 43 and by flexible tongues 40 and 50 which allow the insertion of the reaction cuvette through the upper opening of the chamber, but which prevent removal of the cuvette once the upper end thereof is introduced in chamber 43.

The size of the space available in each chamber 43 of cuvette holder 41 for the upper end portion 34 of a reaction cuvette 31 is chosen large enough to allow displacement of the upper end portion 34 of reaction cuvette in X-, Y-, and Z-direction within chamber 43 and within limits determined by the size of chamber 43. The upper end portion 34 of reaction cuvette 31 and thereby the entire cuvette 31 is thus free to rotate around its length axis 31 within angular limits determined by the size of chamber 43.

Each chamber 43 of cuvette holder 43 has an upper opening, a lower opening. Flexible tongues 40, 50 extend from the upper opening towards the interior of chamber 43. The flexibility of flexible tongues 40, 50 allows the insertion of an entire reaction cuvette 31 through the upper opening of chamber 43, the arrangement of said flexible tongues 40, 50 within chamber 43 prevents withdrawal of cuvette 31 through the upper opening. The lower opening of chamber 43 has a cross-section which is large enough for allowing passage of the body of cuvette 31 through the lower opening of chamber 43, but which prevents passage of the upper portion of cuvette 31 through the lower opening of chamber 43. The upper portion of cuvette 31 including the rigid tongue members 37, 38 is thus retained within chamber 43.

In a preferred embodiment, body 42 of cuvette holder 41 further includes a connecting part 44 adapted for connecting body 42 of cuvette holder 41 to conveyor 11 of the analyzer shown in FIG. 1.

Example of a Cuvette Array

An embodiment of a cuvette array according to the invention is described hereinafter with reference to FIGS. 11-14.

Figure 11:
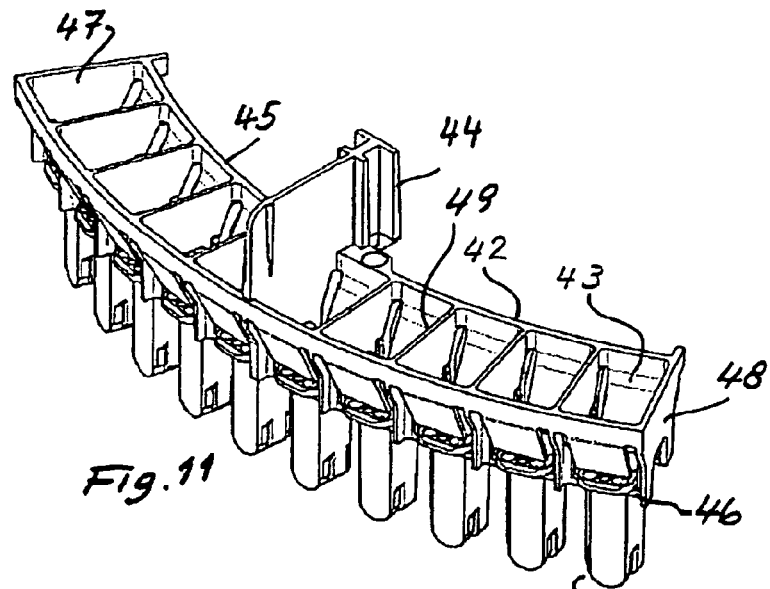
FIG. 11 shows a perspective view of a cuvette array according to the invention comprising a cuvette holder 41 (shown in FIG. 4) and a plurality of cuvettes 31 of the type shown in FIGS. 8-10.
Figure 13:
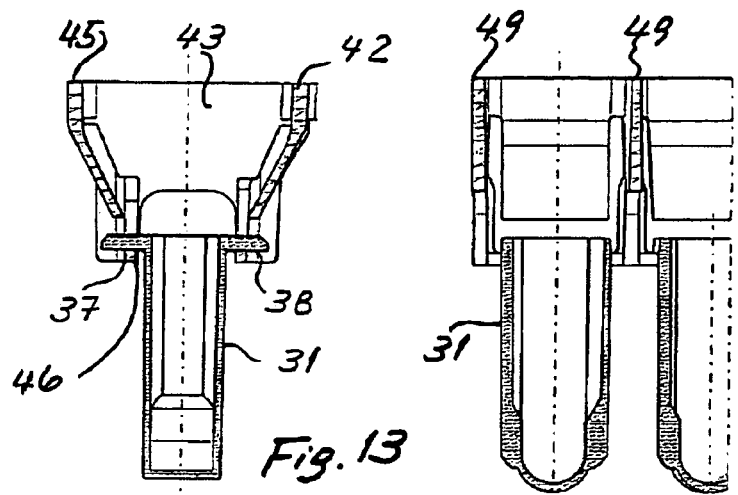
FIG. 13 shows a cross-sectional view taken along a plane C-C in FIG. 12 of a chamber of cuvette holder 41 and of a cuvette 31 held by that chamber.
Figure 14:
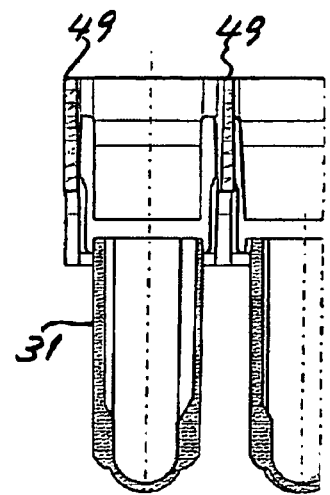
FIG. 14 shows a cross-sectional view taken along a plane D-D in FIG. 12 of a chamber of cuvette holder 41 and of a cuvette 31 held by that chamber.
Figure 12:
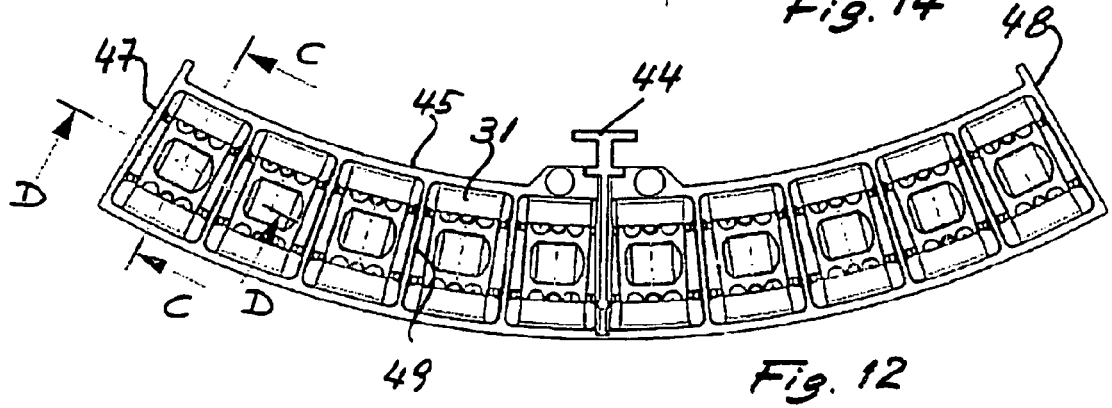
FIG. 12 shows a top plan view of the cuvette array shown in FIG. 11.

FIG. 11 shows a perspective view of a cuvette array according to the invention comprising a cuvette holder 41 (shown in FIG. 4) and a plurality of cuvettes 31 of the type shown in FIGS. 8-10. FIG. 12 shows a top plan view of the cuvette array shown in FIG. 11. FIG. 13 shows a cross-sectional view taken along a plane C-C in FIG. 12 of a chamber of cuvette holder 41 and of a cuvette 31 held by that chamber. FIG. 14 shows a cross-sectional view taken along a plane D-D in FIG. 12 of a chamber of cuvette holder 41 and of a cuvette 31 held by that chamber.

As can be appreciated in particular from FIG. 11, a cuvette array according to the invention comprises a cuvette holder 41 of the above described type and a plurality of reaction cuvettes 31 of the above described type.

As can be appreciated in particular from FIG. 13, the space available for the upper end portion 34 of a reaction cuvette 31 in a chamber 43 of cuvette holder 41 is delimited by intermediate walls 49 which are the side walls of chamber 43 and by flexible tongues 40 and 50 which allow the insertion of the reaction cuvette through the upper opening of chamber 43, but which prevent removal of the cuvette once the upper end portion of the cuvette is introduced into chamber 43.

During the insertion of cuvettes 31 in respective cavities 13 of conveyor 11, are loosely held by cuvette holder 41, but this holder exerts no force or influence on the position each cuvette takes in a cavity 13. The own weight of each cuvette 31 is the only force that acts on it as it is inserted into a cavity 13. The accurate and defined positioning of cuvette 31 in cavity 13 is essentially determined by edges 58 and 59 of the inner surface of bottom wall 56 of cavity 13 and by the close match of shape and dimensions of cuvette 31 and the cavity 13.

Although preferred embodiments of the invention have been described using specific terms, such description is for illustrative purposes only, and it is to be understood that changes and variations may be made without departing from the spirit or scope of the following claims.

What is claimed is:

1. A cuvette holder for holding a plurality of reaction cuvettes, said cuvette holder comprising:
a body extending along a circular segment and defining an array of chambers arranged along a circular segment, each of said chambers having an upper opening, a lower opening, and flexible tongues which extend from said upper opening towards the interior of said chamber, the flexibility of said flexible tongues allowing insertion of an entire reaction cuvette through said upper opening, the arrangement of said flexible tongues within said chamber preventing withdrawal of the cuvette through said upper opening, said lower opening of said chamber having a cross-section which is large enough for allowing passage of the body of said cuvette through said lower opening, but which prevents passage of an upper portion of said cuvette through said lower opening, each of said chambers is for receiving, retaining and holding the entire upper end portion of a reaction cuvette such that the entire upper end portion of the reaction cuvette is allowed to be displaced in X-, Y- and Z-directions within the chamber within limits determined by the size of the chamber.

2. The cuvette holder of claim 1, wherein said body has a connecting part that is for connecting it to a conveyor.

3. A cuvette array comprising
a cuvette holder according to claim 1 and
a plurality of reaction cuvettes, an entire upper end portion of each of said cuvettes being held by said cuvette holder.

4. The cuvette array of claim 3, wherein each of said reaction cuvettes has a rectilinear tubular body which extends between a lower end portion and said upper end portion which lie at opposite ends of said tubular body, said lower end portion being closed by a bottom wall, said upper end portion ending in an opening and including two rigid tongue members adjacent to said opening of said upper end portion, said rigid tongue members extending outwardly from said upper end portion of the tubular body in opposite directions.

5. An automatic analytical apparatus comprising
a rotatable conveyor for conveying reaction cuvettes along a circular path, said conveyor having a first ring shaped body having a circular array of cavities, each cavity is for receiving a single reaction cuvette,
a photometer located adjacent to said rotatable conveyor for carrying out photometric measurements of liquid sample-reagent-mixtures contained in said reaction cuvettes, and
at least one cuvette array that according to claim 3.

6. The automatic analytical apparatus of claim 5, wherein a bottom wall of each of said cavities has two edges which contact and support a bottom wall of a reaction cuvette inserted in said cavity, said edges being parallel to each other and both edges being approximately oriented in radial direction.

7. The automatic analytical apparatus of claim 5, which further comprises
a second ring shaped body having a wall which extends upwardly from an inner side of said first ring shaped body, said wall having openings, each of said openings is for receiving a corresponding connecting part of a cuvette holder that is part of said at least one cuvette array, and
said cuvette holder of said at least one cuvette array having a connecting part which is for connecting it to one of said openings of said wall of said second ring shaped body of said conveyor so that reaction cuvettes held by said cuvette holder are inserted into corresponding cavities of said first ring shaped body of said conveyor.

8. The automatic analytical apparatus of claim 5, which further comprises conveyor driving means for rotating said conveyor in a step-wise manner.

* * * * *

UNITED STATES PATENT AND TRADEMARK OFFICE
CERTIFICATE OF CORRECTION

| | | |
|---|---|---|
| PATENT NO. | : 7,939,036 B2 | Page 1 of 1 |
| APPLICATION NO. | : 11/523837 | |
| DATED | : May 10, 2011 | |
| INVENTOR(S) | : Claudius Burkhardt et al. | |

It is certified that error appears in the above-identified patent and that said Letters Patent is hereby corrected as shown below:

Col. 10, Line 4, "of an upper" should read -- of said upper --

Col. 10, Line 7, "the entire upper" should read -- an entire upper --

Col. 10, Line 37, "cuvette array that" should read -- cuvette array according --

Col. 10, Line 50, "holder that is part" should read -- holder is part --

Signed and Sealed this
Eleventh Day of October, 2011

David J. Kappos
*Director of the United States Patent and Trademark Office*